(12) United States Patent
Segman

(10) Patent No.: US 10,551,298 B2
(45) Date of Patent: Feb. 4, 2020

(54) ARTIFICIAL TISSUE APPARATUS FOR TESTING NON-INVASIVE BIOPARAMETER MEASURING DEVICES

(71) Applicant: Cnoga Medical Ltd., Caesarea (IL)

(72) Inventor: Yosef Segman, Caesarea (IL)

(73) Assignee: CNOGA MEDICAL LTD., Caesarea (IL)

( * ) Notice: Subject to any disclaimer, the term of this patent is extended or adjusted under 35 U.S.C. 154(b) by 0 days.

(21) Appl. No.: 15/905,861

(22) Filed: Feb. 27, 2018

(65) Prior Publication Data
US 2019/0265155 A1    Aug. 29, 2019

(51) Int. Cl.
*G09B 23/28* (2006.01)
*G01N 21/01* (2006.01)
*G01N 33/483* (2006.01)
*G01N 21/17* (2006.01)

(52) U.S. Cl.
CPC ............. *G01N 21/01* (2013.01); *G01N 21/17* (2013.01); *G01N 33/4833* (2013.01)

(58) Field of Classification Search
CPC ............. G01N 2001/2893; G01N 3/62; G01N 33/4833; A61B 6/58; A61B 6/583; A61B 5/0028; A61B 5/0075–0233; A61B 5/1495; G09B 23/28; G01J 2003/006; G01C 25/00
See application file for complete search history.

(56) References Cited

U.S. PATENT DOCUMENTS

| 5,166,517 A * | 11/1992 | Volgyesi | A61B 5/1495 250/252.1 |
| 5,278,627 A * | 1/1994 | Aoyagi | A61B 5/02427 250/252.1 |
| 6,400,973 B1 * | 6/2002 | Winter | A61B 5/1495 600/323 |
| 6,614,521 B2 * | 9/2003 | Samsoondar | A61B 5/1455 356/243.1 |

* cited by examiner

*Primary Examiner* — Rebecca C Bryant
(74) *Attorney, Agent, or Firm* — Mark M. Friedman

(57) ABSTRACT

Apparatus for testing bioparameter monitoring devices includes artificial organs that comprise an elongated sponge wrapped in electrically conductive hydrogel skin, inlet and outlet tubes having a reddish liquid flowing therein and a pulsatile pump configured to generate a pulsatile flow of the liquid. A valve has a variable opening. For each artificial organ: the inlet tube extends out of the sponge and connects eventually to the pulsatile pump, the inlet tube penetrating the elongated sponge so as to extend to a tip of the elongated sponge at a distal end of the inlet tube, and the outlet tube extends out of the elongated sponge and connects eventually to the pulsatile pump at a proximal end of the outlet tube, the outlet tube penetrating the sponge so as to extend to a tip of the elongated sponge at a distal end of the outlet tube.

22 Claims, 7 Drawing Sheets

ARTIFICIAL TISSUE APPARATUS FOR TESTING NON-INVASIVE BIOPARAMETER MEASURING DEVICES

FIELD AND BACKGROUND OF THE INVENTION

The present invention relates to apparatuses and methods for testing bioparameter devices, and more particularly, to apparatuses and methods that include artificial tissue for testing a reliability of non-invasive bioparameter measuring or monitoring devices.

Applicant owns patents and patent applications for non-invasively measuring bioparameters including glucose, oxygen saturation, systolic and diastolic blood pressure, hemoglobin, heart rate, blood viscosity, stroke volume, cardiac output, mean arterial pressure, $PCO_2$, $SPO_2$, $PO_2$, and many others. In order to manufacture these devices, the reliability of these devices needs to be tested efficiently.

SUMMARY OF THE PRESENT INVENTION

One aspect of the present invention is an apparatus for testing a reliability of a batch of noninvasive medical devices, each noninvasive device of the batch having a light source (LED) and at least one optical sensor, each noninvasive device of the batch configured to measure at least one bioparameter of a human subject, the apparatus comprising artificial tissue comprising an elongated sponge wrapped in an electrically conductive hydrogel skin; an inlet tube having a reddish liquid flowing into the inlet tube; an outlet tube having the reddish liquid flowing out of the outlet tube; and a pulsatile pump, including a reciprocating piston, configured to generate a pulsatile flow of the reddish liquid so as to push the reddish liquid into the inlet tube and so as to draw the reddish liquid out of the outlet tube, a valve having a variable opening so as to control how much reddish liquid circulates in the apparatus, the valve positioned between the pulsatile pump and the inlet tube, the inlet tube extending out of the elongated sponge and connecting to the pulsatile pump at a proximal end of the inlet tube, the inlet tube penetrating the elongated sponge so as to extend to a tip of the elongated sponge at a distal end of the inlet tube, the outlet tube extending out of the elongated sponge and connecting to the pulsatile pump at a proximal end of the outlet tube, the outlet tube penetrating the elongated sponge so as to extend to a tip of the elongated sponge at a distal end of the outlet tube.

In some embodiments, the artificial tissue is an artificial finger. In other embodiments, the artificial tissue is an artificial earlobe or a portion of an artificial earlobe.

In some embodiments, the artificial tissue is tapered inwardly in a direction that runs from a proximal end of the artificial tissue to a distal end of the artificial tissue. In some embodiments, the artificial tissue is tapered inwardly from a proximal end of the artificial tissue all the way to a distal end of the artificial tissue.

In some embodiments, the elongated sponge is made of silicone.

In some embodiments, the apparatus is configured to simulate blood flow of a human subject through a finger of the subject.

In some embodiments, the hydrogel is flexible and translucent.

In some embodiments, the artificial finger has an appearance of a human finger.

In some embodiments, the pump has a high enough resolution such that adjustments of a flux of the reddish liquid in the pump generates changes of pressure in the reddish liquid in increments as small as one millimeter mercury.

In some embodiments, the perfusion of the reddish liquid in the sponge simulates nutritive capillary blood flow in a human finger and the perfusion is 50 mL/(100 g*min) plus or minus 25 percent.

In some embodiments, each noninvasive device of the batch is configured to measure at least three bioparameters of a human subject, wherein the three or more bioparameters comprise glucose level, systolic blood pressure, diastolic blood pressure, oxygen saturation, carbon dioxide saturation, hemoglobin, stroke volume, pulse rate, cardiac output and pH.

In some embodiments, each noninvasive device of the batch is configured to measure at least three bioparameters of a human subject, wherein the three or more bioparameters include at least ten bioparameters from among the following: pulse, systolic and diastolic blood pressure, hematocrit, iron, potassium, sodium, nitrogen, red blood cells count, O2 blood concentration and saturation level, blood glucose level, blood CO2 concentration and saturation level, blood pH, blood urea nitrogen level, bilirubin level, stroke volume, stroke volume variation, cardiac output, skin pH, skin color vividness, skin saturation and skin local deformation, oil moisture content of skin, skin dryness, skin pigmentation, red cells concentration, skin saltiness and skin vitality.

Another aspect of the present invention is an apparatus for testing a reliability of a batch of noninvasive medical devices, each noninvasive device of the batch having a light source (LED) and at least one optical sensor, each noninvasive device of the batch configured to measure at least one bioparameter of a human subject, the apparatus comprising a series of artificial organs, each artificial organ comprising (a) an elongated sponge wrapped in an electrically conductive hydrogel skin; (b) an inlet tube having a reddish liquid flowing into the inlet tube; (c) an outlet tube having the reddish liquid flowing out of the outlet tube; and a pulsatile pump, including a reciprocating piston, configured to generate a pulsatile flow of the reddish liquid so as to push the reddish liquid into the inlet tubes and so as to draw the reddish liquid out of the outlet tubes, a valve having a variable opening so as to control how much reddish liquid circulates in the apparatus, the valve positioned between the pulsatile pump and either the inlet tubes or the outlet tubes, for each artificial organ: the inlet tube extends out of the elongated sponge and connects to the pulsatile pump at a proximal end of the inlet tube, the inlet tube penetrating the elongated sponge so as to extend to a tip of the elongated sponge at a distal end of the inlet tube, and the outlet tube extends out of the elongated sponge and connects to the pulsatile pump at a proximal end of the outlet tube, the outlet tube penetrating the elongated sponge so as to extend to a tip of the elongated sponge at a distal end of the outlet tube.

In some embodiments, each artificial organ is configured to test one and only one of the medical devices in the batch of noninvasive medical devices.

In some embodiments, the artificial tissue is an artificial finger. In other embodiments, the artificial tissue is an artificial earlobe or a portion of an artificial earlobe.

In some embodiments, the artificial tissue is tapered inwardly in a direction that runs from a proximal end of the artificial tissue to a distal end of the artificial tissue. In some embodiments, the artificial tissue is tapered inwardly from a proximal end of the artificial tissue all the way to a distal end of the artificial tissue.

In some embodiments, the elongated sponge is made of silicone.

In some embodiments, the hydrogel is flexible and translucent.

In some embodiments, the pump has a high enough resolution such that adjustments of a flux of the reddish liquid in the pump generates changes of pressure in the reddish liquid in increments as small as one millimeter mercury.

In some embodiments, the perfusion of the reddish liquid in the sponge simulates nutritive capillary blood flow in a human finger and the perfusion is 50 mL/(100 g*min) plus or minus 25 percent.

In some embodiments, each noninvasive device of the batch is configured to measure at least three bioparameters of a human subject, wherein the three or more bioparameters comprise glucose level, systolic blood pressure, diastolic blood pressure, oxygen saturation, carbon dioxide saturation, hemoglobin, stroke volume, pulse rate, cardiac output and pH.

In some embodiments, each noninvasive device of the batch is configured to measure at least three bioparameters of a human subject, wherein the three or more bioparameters include at least ten bioparameters from among the following; pulse, systolic and diastolic blood pressure, hematocrit, iron, potassium, sodium, nitrogen, red blood cells count, O2 blood concentration and saturation level, blood glucose level, blood CO2 concentration and saturation level, blood pH, blood urea nitrogen level, bilirubin level, stroke volume, stroke volume variation, cardiac output, skin pH, skin color vividness, skin saturation and skin local deformation, oil moisture content of skin, skin dryness, skin pigmentation, red cells concentration, skin saltiness and skin vitality.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

Figure 1:
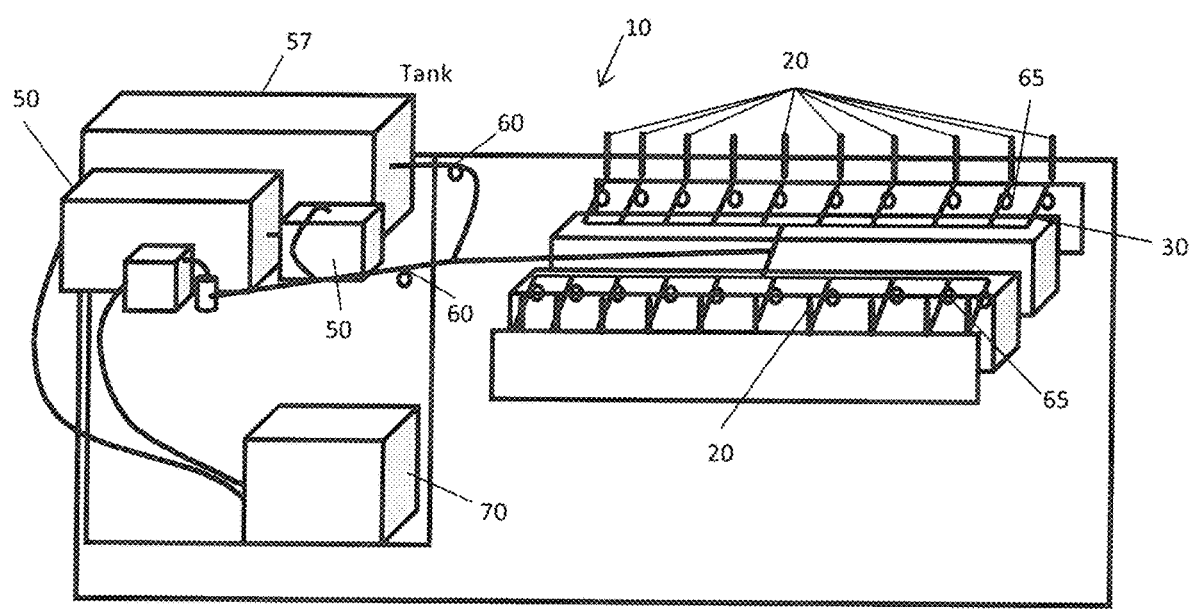
FIG. 1 is a schematic of an apparatus, in accordance with one embodiment of the invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The invention generally provides an apparatus, including artificial tissue, for testing non-Invasive bioparameter measuring devices, typically devices that have a light source and at least one optical sensor. The artificial finger and related apparatus is used to efficiently test and establish a reliability of a plurality of identical devices, each device configured to measure at least one bioparameter, typically a number of bioparameters, in one embodiment more than three bioparameters, in another embodiment more than a dozen bioparameters and in another embodiment approximately twenty bioparameters, of a human or other mammalian subject noninvasively.

The present invention is an apparatus for efficiently testing a reliability of a batch of noninvasive medical devices, each noninvasive device of the batch having a light source (LED) and at least one optical sensor, each noninvasive device of the batch configured to measure at least one bioparameter of a mammalian subject, for example a human subject, and in some embodiments at least two and in some embodiments at least three and in some embodiments about twenty bioparameters of the human subject. The testing of the noninvasive medical devices is to establish a reliability of the batch of medical devices. For example the testing may be used during a quality control procedure during the manufacturing of the devices. If for example, all except some minority, purely by way of example twenty percent, of a batch of the non-invasive medical devices tested output an identical level of each bioparameter that the devices monitor (i.e. blood pressure, pulse etc.), wherein identical is defined to be within a pre-established threshold of deviation, then the other eighty percent of the batch of devices are deemed to have passed the quality control procedure and the twenty percent of the devices are deemed to have failed the quality control procedure. Note that the above percentages 80%/20% are purely illustrative and non-limiting.

The principles and operation of an Artificial Tissue Apparatus for Testing Non-Invasive Bioparameter Measuring Devices may be better understood with reference to the drawings and the accompanying description.

In one embodiment, an apparatus 10 for testing a reliability of at least one noninvasive medical device, and typically a batch of noninvasive medical devices, is presented wherein each noninvasive device of the batch typically has a light source (LED) and at least one optical sensor. Each noninvasive device of the batch is also configured to measure at least one bioparameter of a human subject. The batch of non-invasive devices is a batch of identical devices in some embodiments.

As shown by FIG. 1-6, the apparatus 10 may comprise at least one artificial tissue 20, typically a series of such individual artificial tissue elements 20, which may be organs such as artificial fingers 20. FIG. 1 depicts an apparatus that includes twenty artificial fingers 20a, 20b, 20c, 20d, 20e, . . . 20t. The fingers 20a . . . 20t are essentially identical because they are designed to test devices being manufactured that are designed to be identical to one another. In one particular non-limiting embodiment, each artificial tissue 20, for example each artificial organ 20, is configured to test one and only one of the non-invasive medical devices in the batch of noninvasive medical devices. Because FIG. 1 is merely schematic, it does not depict both an inlet tube 30 and outlet tube 40 running from each of the twenty artificial fingers 20a, 20b, 20c, 20d, 20e, . . . 20t shown in the figure, but rather just generically shows a tube for each finger 20a . . . 20t, which tube has for convenience been labeled inlet tube 30. The quantity twenty is non-limiting and is designed to test the reliability of a batch of twenty non-invasive devices.

The non-invasive devices operate by inserting one's finger or earlobe or other tissue into a recess in the device whereupon the light source and the at least one optical sensor operate to take at least one image of the tissue. In other embodiments, the non-invasive devices operate by placing the tissue alongside a surface of the non-invasive device and may also involve covering the tissue. Accordingly, each artificial tissue 20, for example artificial finger 20 or artificial earlobe 20, is configured to be tested by being inserted into a recess in the non-invasive device just as an actual finger or earlobe or other tissue would be. In some embodiments, the artificial tissue 20 is configured to be placed alongside a surface of the non-invasive device and may also involve covering the tissue.

Figure 2:
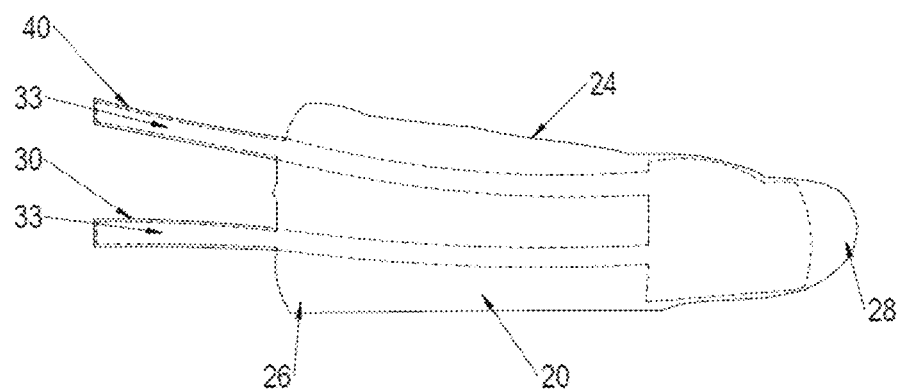
FIG. 2 is a photo showing a perspective view of an artificial finger, in accordance with one embodiment of the invention.

As shown in a closer view in FIG. 2, each such artificial tissue 20 may comprise an elongated sponge 22 that may be wrapped in an electrically conductive hydrogel skin 24. An example of a material used for sponge 22 is silicone. In other embodiments, certain other porous materials that behave like a sponge may also be used as the material for sponge 22. In some embodiments, sponge 22 is made from Sylgard® 184 Silicone Elastomer manufactured by Dow Corning®, a company headquartered in Midland, Mich. An example of the hydrogel 24 used in the hydrogel skin is a polymeric hydrogel. In some embodiments, the hydrogel 24 skin is flexible and translucent.

One of the characteristics of real human skin is that it is electrically conductive, unless the skin is damaged from being too dry. Since artificial tissue 20 is designed to simulate actual human tissue (or other mammalian tissue), such as an organ that includes a surface comprising normal skin tissue, polymeric hydrogel is an appealing material for the skin 24 that sponge 22 is wrapped in because hydrogel is electrically conductive, a property of normal skin tissue.

Figure 5:
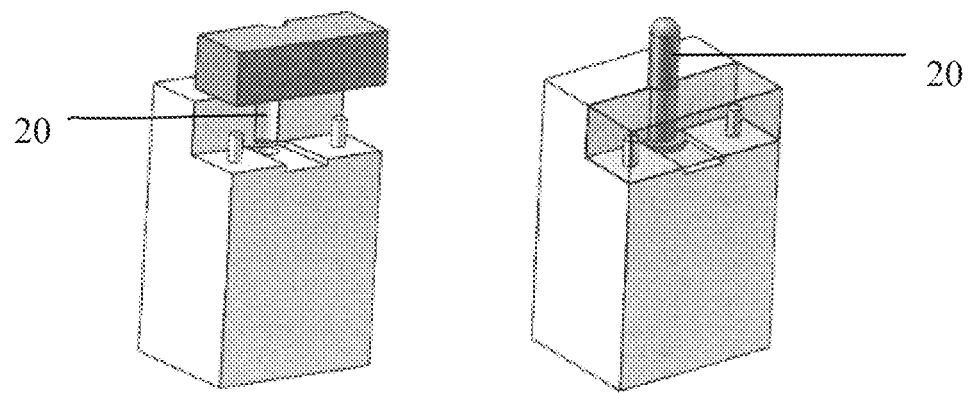
FIG. 5 is a schematic showing 3D printing of artificial fingers, in accordance with one embodiment of the invention.

In some embodiments, artificial tissue 20 is tapered inwardly in a direction that runs from a proximal end 26 of the artificial tissue 20 to a distal end 28 of the artificial tissue 20. For example, in some embodiments as shown in FIG. 2 and partially shown in FIG. 4B, artificial finger 20 may be tapered inwardly from a proximal end 26 of artificial tissue 20 all the way to distal end 28 of artificial tissue 20. Although FIG. 4B only shows the tapering schematically in certain parts of the length of artificial finger 20, this figure is not intended to show the actual degree of tapering or its precise location. Accordingly, although FIG. 4B does not depict the inward tapering in a middle area of the length of artificial tissue 20, in some embodiments the inward tapering runs all or substantially all of the length of tissue 20 from proximal end 26 of artificial tissue 20 all the way to distal end 28 of artificial tissue 20 (including any middle area of the length of tissue 20). For example, FIG. 2 shows inward tapering along substantially all of the length of tissue 20 from proximal end 26 to distal end 28. In one particular embodiment, the tapering of artificial tissue 20 mimics or substantially mimics the tapering (i.e. changing width) of a middle finger of a human hand and in another embodiment it mimics or substantially mimics the tapering of a pointer finger of a human hand. As shown in FIG. 5, in some embodiments, artificial tissue 20 is manufactured using 3D printing technology.

In other embodiments (other than embodiments where artificial tissue 20 is an artificial finger 20), artificial tissue element 20 is an artificial earlobe or a portion of an artificial earlobe. Apparatus 10 is also usable for other organs besides fingers and earlobes. The shape of sponge 22 and the shape of the artificial organ 20 is configured in each case to sufficiently simulate the shape of the real organ as necessary to implement the invention. In some cases, therefore, sponge 22 may not be elongated.

As seen from FIG. 1, FIG. 2, FIG. 4A and FIG. 4B (and FIG. 6), in one particular embodiment, each artificial tissue element 20 has associated with it an inlet tube 30 having a fluid such as a liquid 33, for example a reddish liquid 33, flowing into the inlet tube as well as an outlet tube 40 having the fluid such as a liquid, for example reddish liquid 33 flowing out of the outlet tube 40. The inlet tube 30 may extend out of the elongated sponge 22 and may connect in some embodiments to a more central inlet tube 30 or tubes 30 and eventually to the pulsatile pump 50 at a proximal end 31 of the inlet tube 30 or tubes 30. The inlet tube 30 in some embodiments penetrates the elongated sponge 22 so as to extend to a tip 23 of the elongated sponge 22 at a distal end 32 of the inlet tube 30, the outlet tube 40 extending out of the elongated sponge 22 and connecting in some embodiments to a more central outlet tube 40 or tubes 40 and eventually to the pulsatile pump 50 or to a tank 57 of the pulsatile pump 50 (tank 57 is considered part of the overall pump 50) at a proximal end 41 of the outlet tube 40 or tubes 40, the outlet tube 40 penetrating the elongated sponge 22 so as to extend to a tip 23 of the elongated sponge 22 at a distal end 42 of the outlet tube 40.

It is understood that, particularly from the area outside the artificial tissue 20 running from the artificial tissue 20 to the pump 50, inlet tube 30 may include multiple inlet tubes 20. Likewise, it is understood that, particularly from the area outside the artificial tissue 20 running from the artificial tissue 20 to the pump 50, outlet tube 40 may include multiple outlet tubes 40.

In some embodiments, reddish liquid 33 comprises a liquid that simulates blood of a mammalian subject such as a human subject, by comprising blood plasma plus artificial coloring. In certain embodiments, in order to simulate blood plasma, reddish liquid 33 is a liquid that holds various added substances 34 in suspension therein like real blood plasma does. In some embodiments, reddish liquid 33 also has within it an added substance 34. The added substance 34 may be dissolved wholly or partly in reddish liquid 34 and is designed to assist in imitating or simulating mammalian blood, for example human blood, for example live human blood in vivo. Some examples of the added substance(s) 34 include a gas such as oxygen, carbon dioxide, nitrogen, etc. Other examples of substance(s) 34 include glucose or one or more of various minerals such as sodium, potassium, etc.

The term "reddish" as used in this patent application as a description of a colored object is understood to not only include objects that look reddish but also objects that look red.

The viscosity of reddish liquid 33 is designed to simulate the blood flow and blood ingredients of mammalian blood such as human blood. The reason liquid 33 is reddish is that the at least one optical sensor of the noninvasive device in actual use take an image of the real tissue, which includes real blood, and because for the testing process one wants the noninvasive devices to obtain a bioparameter reading from the artificial tissue 20 that is as close as possible to the bioparameter reading that would be obtained is actual in vivo mammalian tissue (such as human tissue) were used.

Figure 3:
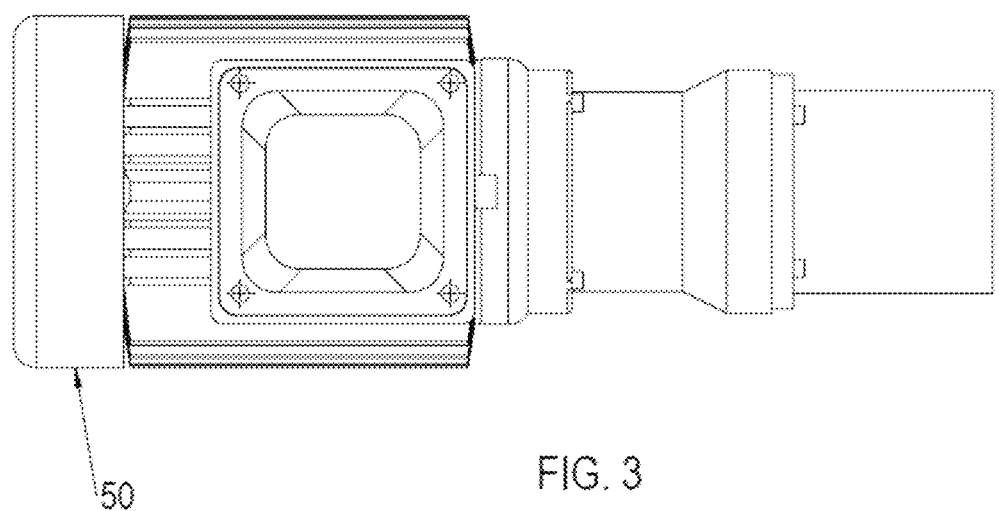
FIG. 3 is a photo of a pump used in the artificial finger, in accordance with one embodiment of the invention.
Figure 4A:
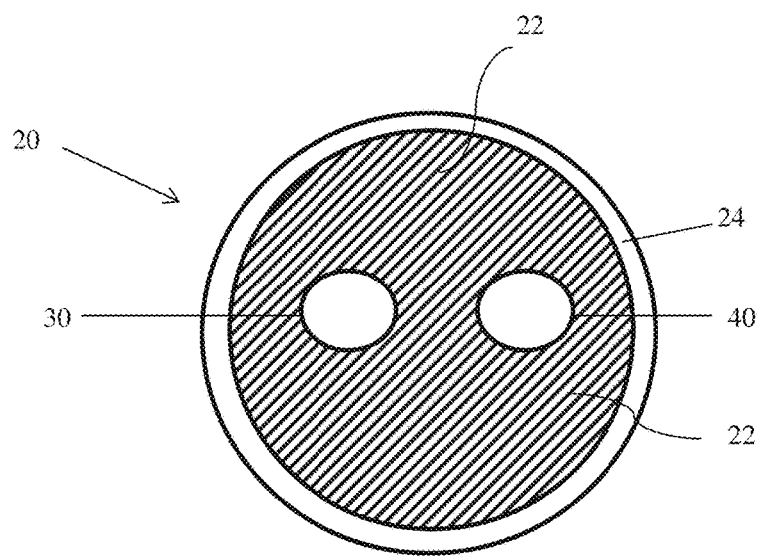
FIG. 4A is a schematic illustration showing a horizontal sectional view of the inside of an artificial finger, in accordance with one embodiment of the invention.
Figure 4B:
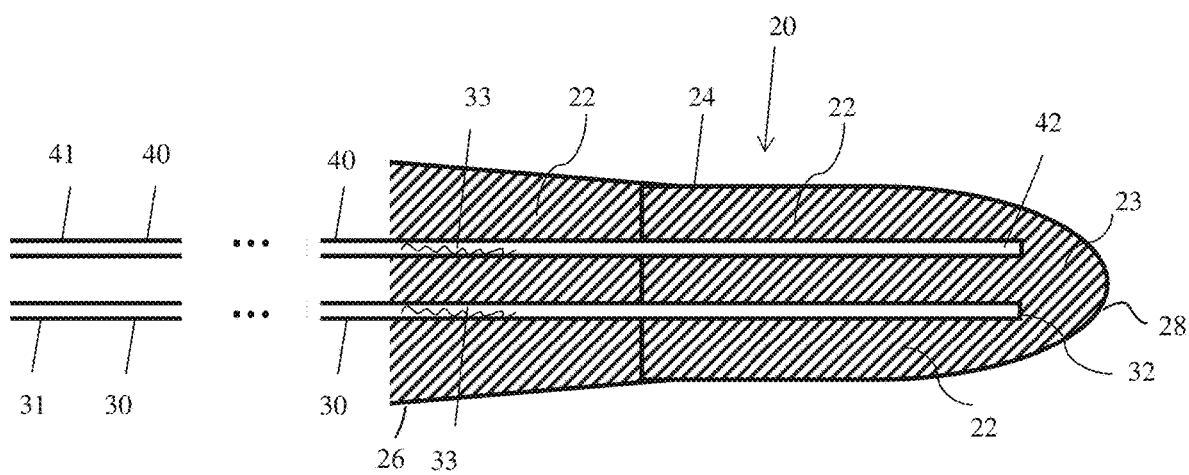
FIG. 4B is a schematic illustration of a vertical sectional view of an artificial finger, in accordance with one embodiment of the invention.
Figure 6:
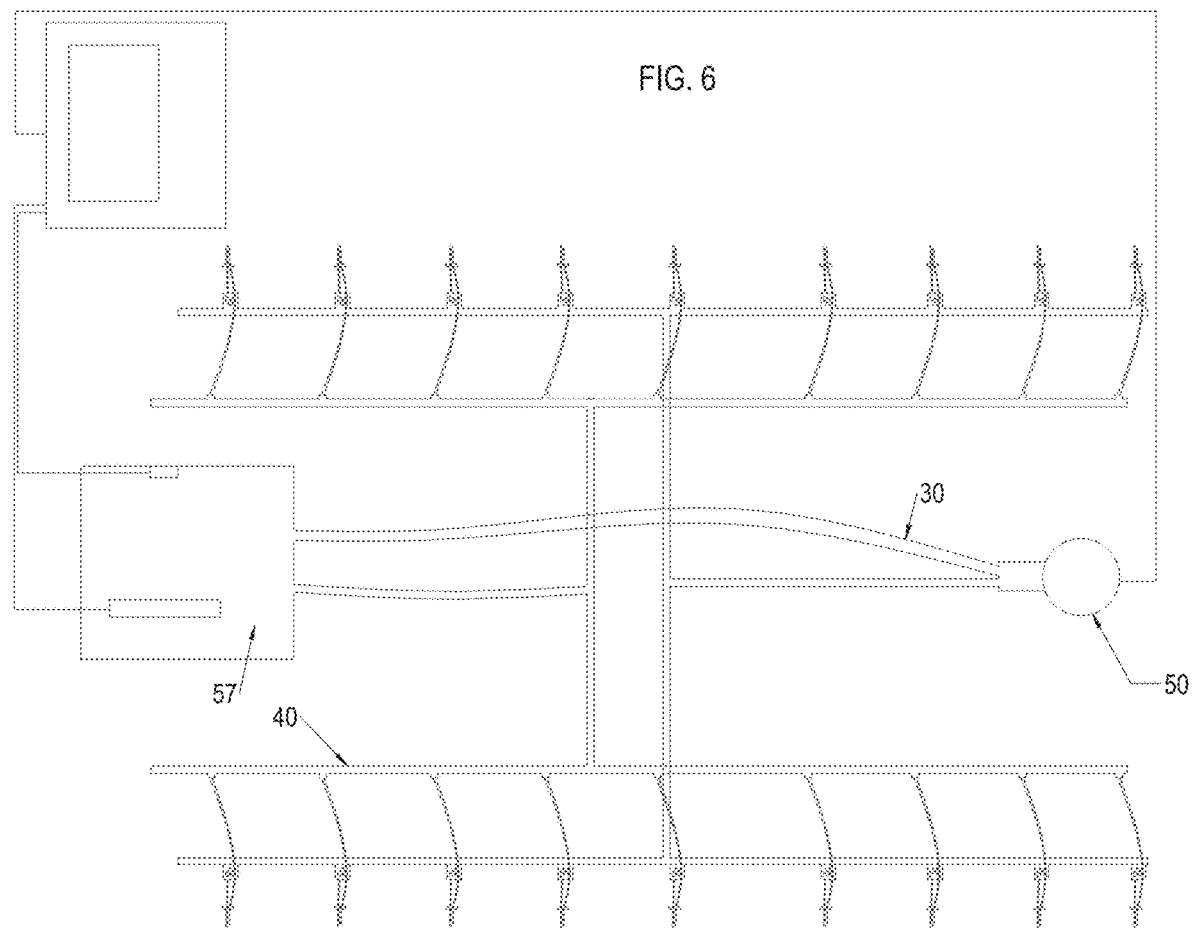
FIG. 6 is a further configuration of parts of the apparatus, in accordance with one embodiment of the invention.

As shown in FIG. 1, FIG. 3 and FIG. 6, apparatus 10 includes a pulsatile pump 50 designed to simulate a heart of a mammalian subject such as a human. Apparatus 10 may also comprise an electric power supply (not shown) for the pump 50.

Pump 50 may include a reciprocating piston 52, configured to generate a pulsatile flow of the reddish liquid 33 so as to push the reddish liquid 33 into the inlet tube 30 and so as to draw the reddish liquid 33 out of the outlet tube 40.

Figure 1A:
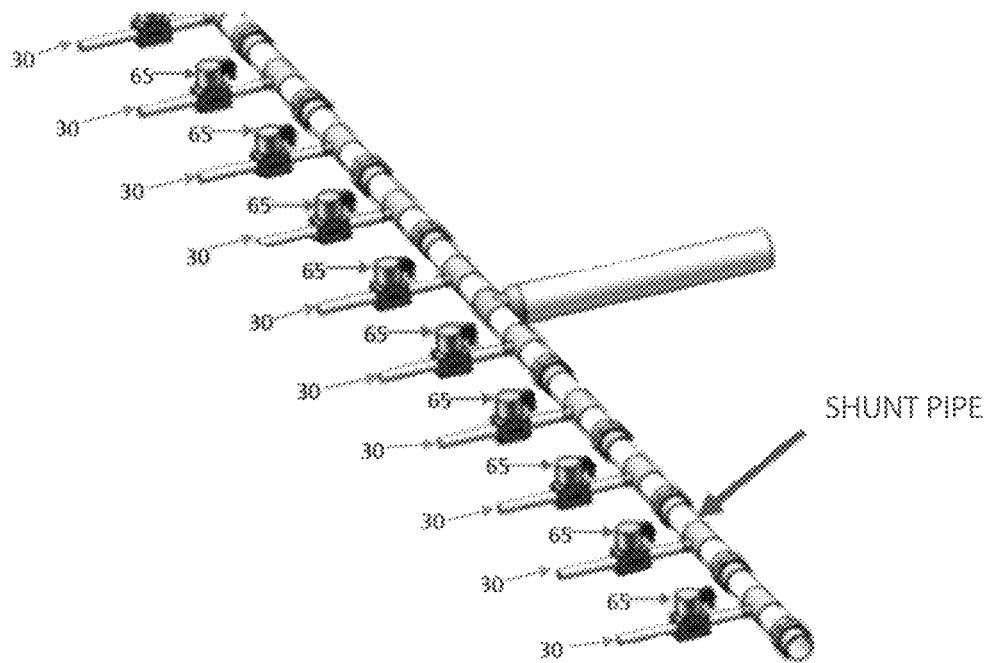
FIG. 1A is a photo of a series of valves controlling tubes directing leading into individual artificial fingers, in accordance with one embodiment of the invention.

As seen in FIG. 1 and FIG. 1A, apparatus 10 may also comprise a valve 60 having a variable opening 62 so as to control how much reddish liquid 33 circulates in the apparatus 10. Valve 60 is a central valve 60 and may be positioned on a central pipe or tube that leads from the pulsatile pump 50 to the inlet tubes 30 and/or in some embodiments on a central pipe that leads from the pulsatile pump 50, for example a tank 57 of the pump 50, and the outlet tubes 40. More than one valve 60 may be positioned in some embodiments. In certain embodiments, as seen in FIG. 1 and in FIG. 6, there are also individual valves 65a, 65b, 65c, 65d, 65e . . . 65t on each tube or pipe that leads to each individual artificial tissue 20. The individual valves allow the user to control or shut off liquid 33 flow to an individual artificial tissue 20 among the series of artificial tissue elements. FIG. 6 is a photo of parts of apparatus 10 having a different configuration to provide a better view of the valves and tubes but without showing the artificial tissue 20.

As shown in FIG. 1, apparatus 10 may also include a control module 70 for directing the valves 60 and the pump 50.

The invention, in one embodiment, is an apparatus 10 for testing a reliability of a batch of noninvasive medical devices, each noninvasive device of the batch having a light source (LED) (not shown) and at least one optical sensor (not shown), each noninvasive device of the batch configured to measure at least one bioparameter of a human subject. Apparatus 10 comprises a series of artificial organs 20, each artificial organ 20 comprising (a) an elongated sponge 22 wrapped in an electrically conductive hydrogel skin 24; (b) an inlet tube 30 having a reddish liquid 33 flowing into the inlet tube 30; and (c) an outlet tube 40 having the reddish liquid 33 flowing out of the outlet tube 40.

Apparatus 10 may further comprise a pulsatile pump 50, which may include a reciprocating piston (not specifically shown), configured to generate a pulsatile flow of the reddish liquid 33 so as to push the reddish liquid 33 into the inlet tubes 30 and so as to draw the reddish liquid out of the outlet tubes 40. Apparatus 10 may further comprise a valve 50 having a variable opening (not shown) so as to control how much reddish liquid 33 circulates in the apparatus, the valve 50 positioned between the pulsatile pump 50 and the inlet tubes 30 (or between the pump and the outlet tubes 40).

In one embodiment, as seen in FIG. 1, FIG. 2, FIG. 4A and FIG. 4B (and FIG. 6), for each artificial organ 20 in the series of artificial organs the following is: the inlet tube 30 extends out of the elongated sponge 22 and connects to a more central inlet tube 30 in some embodiments and eventually to the pulsatile pump 50 at a proximal end 31 of the inlet tube 30, the inlet tube 30 penetrating the elongated sponge so as to extend to a tip 23 of the elongated sponge at a distal end 32 of the inlet tube 30, and the outlet tube 40 extends out of the elongated sponge 22 and connects in some embodiments to a more central outlet tube 40 and eventually to the pulsatile pump 50 or to a tank 57 of the pulsatile pump 50 at a proximal end 41 of the outlet tube 40, the outlet tube 40 penetrating the elongated sponge 22 so as to extend to a tip 23 of the elongated sponge 22 at a distal end 42 of the outlet tube 40.

The total volume of artificial blood circulated in apparatus 10 is the total volume in cubic centimeters (cc) of artificial blood, for example reddish liquid 33, injected through the main valve 60 multiplied by the number of pulses (corresponding to beats of a heart) generated by the pump 50. The total volume is considered an artificial cardiac output of the system, in this case of apparatus 10.

The elongated sponge 22 has the effect of simulating the capillaries of the human finger. Accordingly, the pump 50 and the inlet tubes 30 and outlet tubes 40, together with the sponge 22 simulate the artificial blood vessels including the artificial capillaries, of the entire system so as to generate a local artificial blood pressure. As a result of the pulsatile pump 50 and the inlet and outlet tubes 30, 40, the local pressure in various locations within apparatus 10 simulate the local blood pressure including a local artificial systolic and a local artificial diastolic pressure.

In any embodiment, apparatus 10 is configured to simulate blood flow of a human subject through an artificial tissue, for example an artificial finger 20, of the subject. In all, apparatus 10 is designed so that artificial finger 20 has an appearance of a human finger.

Pump 50 is designed with a high enough resolution such that adjustments of a flux of the reddish liquid 33 in the pump 50 generates changes of pressure in the reddish liquid 33 in increments as small as half a millimeter Hg or in some embodiments as small as one millimeter Hg, or in some embodiments as small as two millimeters Hg, or in some embodiments as small as three mm Hg, or as small as 4 mm Hg, 5 mm Hg, 6 mm Hg, 7 mm Hg, 8 mm Hg 9 mm Hg or ten mm Hg or 11 mm Hg or 12 mm Hg or 13 mm Hg or 14 mm Hg or 15 mm Hg or 16 mm Hg or 17 mm Hg or 18 mm Hg or 19 mm Hg or 20 mm Hg or 30 mm Hg or 40 mm Hg or 50 mm Hg or 60 mm Hg or another number suitable as an incremental change in blood pressure. In some embodiments, the perfusion of the reddish liquid 33 in the sponge 22 and in artificial tissue 20 simulates nutritive capillary blood flow in a human finger. In certain embodiments, the perfusion of reddish liquid 33 in artificial tissue 20 and in sponge 22 is 50 mL/(100 g*min) or another amount somewhere in a range of ten percent more or less than 50 mL/(100 g*min), or in another embodiments somewhere in a range of 20% or 25% or 30% or 50% or 70% more or less than 50 mL/(100 g*min).

As noted, the non-invasive medical devices (not shown) are configured to measure at least one bioparameter of a mammalian subject. In some embodiments of apparatus 10 or method 100, the devices are configured to measure at least one bioparameter. The bioparameters of the at least one bioparameter are classified into four groups of bioparameters: hemodynamic, hematological bioparameters, blood gases, biochemistry bioparameters, where hemodynamic bioparameters is the group of bioparameters related to blood flow such as pulse, blood pressure (systolic and diastolic), stroke volume, cardiac output, etc. Hematology is considered the group of bioparameters that include hemoglobin, red blood count, hematocrit, platelets, etc. Blood gases is considered the group of bioparameters that include carbon dioxide concentration, carbon dioxide saturation, oxygen concentration, oxygen saturation, pH, etc. Biochemistry is considered the group of bioparameters that includes glucose, nitrogen, iron, potassium, sodium, etc. In other embodiments, the devices are configured to measured three or more bioparameters. In one particular embodiment, the three or more bioparameters include at least ten or at least twelve or at least fifteen or at least twenty or in other embodiments approximately twenty bioparameters from among the following; pulse, systolic and diastolic blood pressure, red blood cells count, $O_2$ blood saturation level, blood glucose level, blood CO2 level, blood pH, blood urea nitrogen level, bilirubin level, Oxygen and carbon dioxide concentration, stroke volume or stroke volume variation, cardiac output, skin pH, skin color vividness, skin saturation and skin local deformation, oil moisture content of skin, skin dryness, skin pigmentation, red cells concentration, skin saltiness, skin vitality. In one particular non-limiting embodiment, the at least one bioparameters includes at least one bioparameter from each of the four groups of bioparameters (hemodynamic, hematological bioparameters, blood gases, biochemistry).

One embodiment of the invention is an artificial organ 20, comprising artificial tissue 20 comprising an elongated sponge 22 wrapped in an electrically conductive hydrogel skin 24; an inlet tube 30 having a reddish liquid 33 flowing into the inlet tube 30; an outlet tube 40 having the reddish liquid 33 flowing out of the outlet tube 40; and a pulsatile pump 50 configured to generate a pulsatile flow of the reddish liquid 33 so as to push the reddish liquid 33 into the inlet tube 30 and so as to draw the reddish liquid 33 out of the outlet tube 40, the inlet tube 30 extending out of the elongated sponge 22 and connecting to the pulsatile pump 50 at a proximal end 31 of the inlet tube 32, the inlet tube 30 penetrating the elongated sponge 22 so as to extend to a tip 23 of the elongated sponge 22 at a distal end 32 of the inlet tube 30, the outlet tube 40 extending out of the elongated sponge 22 and connecting to the pulsatile pump 50 (for example to a tank 57 of the pump 50) at a proximal end 41 of the outlet tube 42, the outlet tube 40 penetrating the elongated sponge 22 so as to extend to a tip 23 of the elongated sponge 22 at a distal end 42 of the outlet tube 40.

Any suitable feature mentioned herein in respect to the embodiments of apparatus 10 that comprises a single artificial tissue 20 may also be incorporated into the embodiments of apparatus 10 that comprise the series of artificial tissue 20 elements discussed herein. Similarly, any suitable feature mentioned herein in respect to the embodiments of apparatus 10 that comprises multiple or a series of artificial tissue 20 elements may also be incorporated into the embodiments of apparatus 10 that comprise a single artificial tissue 20.

Figure 7:
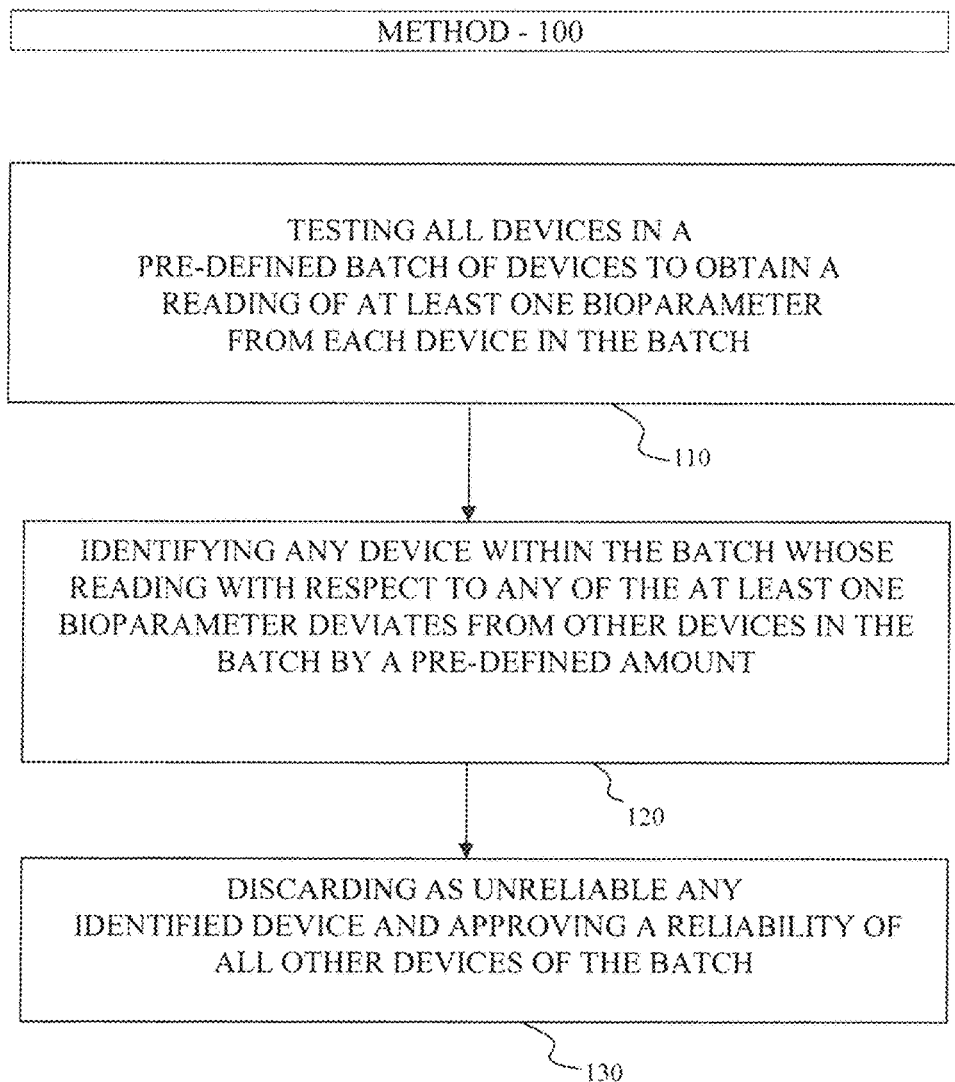
FIG. 7 is a flow chart showing a method, in accordance with one embodiment of the invention.

As seen from FIG. 7, one embodiment of the invention is a method 100 of testing a reliability of a plurality of devices, wherein each device has a light source (LED) and an optical sensor, the devices configured to measure at least one bioparameter of a human subject. The type of bioparameters are those discussed in regard to the at least one bioparameter for apparatus 10. Method 100 may comprise a step 110 of testing all devices in a pre-defined batch of devices to obtain a reading of at least one bioparameter from each device in the batch.

Method 100 may also comprise a step 120 of identifying any device within the batch whose reading with respect to any of the at least one bioparameter deviates from other devices in the batch by a pre-defined amount. This may be performed by placing each non-invasive device on each artificial tissue. Method 100 may further comprise a step 130 of discarding as unreliable any identified device and approving a reliability of all other devices of the batch.

Method 100 may in some embodiments utilize any component or feature described herein in connection with apparatus 10. For example, step 110 of method 100 may involve using an apparatus that has many or all or the features of apparatus 10 to test the non-invasive devices.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. Apparatus for testing a reliability of a batch of noninvasive medical devices, each noninvasive device of the batch having a light source (LED) and at least one optical sensor, each noninvasive device of the batch configured to measure at least one bioparameter of a human subject, the apparatus comprising:
   artificial tissue comprising an elongated sponge wrapped in an electrically conductive hydrogel skin;
   an inlet tube having a reddish liquid flowing into the inlet tube;
   an outlet tube having the reddish liquid flowing out of the outlet tube; and
   a pulsatile pump, including a reciprocating piston, configured to generate a pulsatile flow of the reddish liquid so as to push the reddish liquid into the inlet tube and so as to draw the reddish liquid out of the outlet tube,
   a valve having a variable opening so as to control how much reddish liquid circulates in the apparatus, the valve positioned between the pulsatile pump and the inlet tube, the inlet tube extending out of the elongated sponge and connecting to the pulsatile pump at a proximal end of the inlet tube, the inlet tube penetrating the elongated sponge so as to extend to a tip of the elongated sponge at a distal end of the inlet tube, the outlet tube extending out of the elongated sponge and connecting to the pulsatile pump at a proximal end of the outlet tube, the outlet tube penetrating the elongated sponge so as to extend to a tip of the elongated sponge at a distal end of the outlet tube.

2. The apparatus of claim 1, wherein the artificial tissue is an artificial finger.

3. The apparatus of claim 1, wherein the artificial tissue is an artificial earlobe or a portion of an artificial earlobe.

4. The apparatus of claim 1, wherein the artificial tissue is tapered inwardly in a direction that runs from a proximal end of the artificial tissue to a distal end of the artificial tissue.

5. The apparatus of claim 1, wherein the artificial tissue is tapered inwardly from a proximal end of the artificial tissue all the way to a distal end of the artificial tissue.

6. The apparatus of claim 1, wherein the elongated sponge is made of silicone.

7. The apparatus of claim 1, wherein the apparatus is configured to simulate blood flow of a human subject through a finger of the subject.

8. The apparatus of claim 1, wherein the hydrogel is flexible and translucent.

9. The apparatus of claim 1, wherein the artificial finger has an appearance of a human finger.

10. The apparatus of claim 1, wherein the pump has a high enough resolution such that adjustments of a flux of the reddish liquid in the pump generates changes of pressure in the reddish liquid in increments as small as one millimeter mercury.

11. The apparatus of claim 1, wherein the perfusion of the reddish liquid in the sponge simulates nutritive capillary blood flow in a human finger and the perfusion is 50 mL/(100 g*min) plus or minus 25 percent.

12. The apparatus of claim 1, each noninvasive device of the batch is configured to measure at least three bioparameters of a human subject, wherein the three or more bioparameters comprise glucose level, systolic blood pressure, diastolic blood pressure, oxygen saturation, carbon dioxide saturation, hemoglobin, stroke volume, pulse rate, cardiac output and pH.

13. The apparatus of claim 12, each noninvasive device of the batch is configured to measure at least three bioparameters of a human subject, wherein the three or more bioparameters include at least ten bioparameters from among the following; pulse, systolic and diastolic blood pressure, hematocrit, iron, potassium, sodium, nitrogen, red blood cells count, O2 blood concentration and saturation level, blood glucose level, blood CO2 concentration and saturation level, blood pH, blood urea nitrogen level, bilirubin level, stroke volume, stroke volume variation, cardiac output, skin pH, skin color vividness, skin saturation and skin local deformation, oil moisture content of skin, skin dryness, skin pigmentation, red cells concentration, skin saltiness and skin vitality.

14. Apparatus for testing a reliability of a batch of noninvasive medical devices, each noninvasive device of the batch having a light source (LED) and at least one optical sensor, each noninvasive device of the batch configured to measure at least one bioparameter of a human subject, the apparatus comprising:
  a series of artificial organs, each artificial organ comprising
    (a) an elongated sponge wrapped in an electrically conductive hydrogel skin;
    (b) an inlet tube having a reddish liquid flowing into the inlet tube;
    (c) an outlet tube having the reddish liquid flowing out of the outlet tube; and
  a pulsatile pump, including a reciprocating piston, configured to generate a pulsatile flow of the reddish liquid so as to push the reddish liquid into the inlet tubes and so as to draw the reddish liquid out of the outlet tubes,
  a valve having a variable opening so as to control how much reddish liquid circulates in the apparatus, the valve positioned between the pulsatile pump and either the inlet tubes or the outlet tubes,
  for each artificial organ:
  the inlet tube extends out of the elongated sponge and connects to the pulsatile pump at a proximal end of the inlet tube, the inlet tube penetrating the elongated sponge so as to extend to a tip of the elongated sponge at a distal end of the inlet tube, and
  the outlet tube extends out of the elongated sponge and connects to the pulsatile pump at a proximal end of the outlet tube, the outlet tube penetrating the elongated sponge so as to extend to a tip of the elongated sponge at a distal end of the outlet tube.

15. The apparatus of claim 14, wherein each artificial organ is configured to test one and only one of the medical devices in the batch of noninvasive medical devices.

16. The apparatus of claim 14, wherein the artificial tissue is an artificial finger.

17. The apparatus of claim 14, wherein the artificial tissue is an artificial earlobe or a portion of an artificial earlobe.

18. The apparatus of claim 14, wherein the artificial tissue is tapered inwardly in a direction that runs from a proximal end of the artificial tissue to a distal end of the artificial tissue.

19. The apparatus of claim 14, wherein the elongated sponge is made of silicone.

20. The apparatus of claim 14, wherein the hydrogel is flexible and translucent.

21. The apparatus of claim 14, wherein the pump has a high enough resolution such that adjustments of a flux of the reddish liquid in the pump generates changes of pressure in the reddish liquid in increments as small as one millimeter mercury.

22. The apparatus of claim 14, wherein the perfusion of the reddish liquid in the sponge simulates nutritive capillary blood flow in a human finger and the perfusion is 50 mL/(100 g*min) plus or minus 25 percent.

* * * * *